United States Patent
Tokumaru et al.

(10) Patent No.: US 9,347,858 B2
(45) Date of Patent: May 24, 2016

(54) DISPENSING DEVICE AND DISPENSING SYSTEM

(71) Applicant: Panasonic Healthcare Holdings Co., Ltd., Tokyo (JP)

(72) Inventors: Tomoyoshi Tokumaru, Gunma (JP); Takahiro Inoue, Kyoto (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 176 days.

(21) Appl. No.: 14/039,953

(22) Filed: Sep. 27, 2013

(65) Prior Publication Data

US 2014/0030168 A1 Jan. 30, 2014

Related U.S. Application Data

(63) Continuation of application No. PCT/JP2011/079826, filed on Dec. 22, 2011.

(30) Foreign Application Priority Data

Mar. 28, 2011 (JP) .................. 2011-070595
Mar. 28, 2011 (JP) .................. 2011-070596

(51) Int. Cl.
*B01L 3/02* (2006.01)
*G01N 1/14* (2006.01)
*G01N 35/10* (2006.01)

(52) U.S. Cl.
CPC . *G01N 1/14* (2013.01); *B01L 3/021* (2013.01); *G01N 35/1016* (2013.01); *B01L 2400/0457* (2013.01); *B01L 2400/0487* (2013.01); *B01L 2400/0633* (2013.01); *G01N 2035/1034* (2013.01)

(58) Field of Classification Search
CPC ................... G01N 35/1011; G01N 33/48728; C12N 5/0612; C12N 5/061; B01L 3/0241
USPC .............. 422/500–502, 509, 73; 347/46, 68; 436/180
See application file for complete search history.

(56) References Cited

U.S. PATENT DOCUMENTS

| 3,815,786 A | 6/1974 | McCallum |
| 2002/0011276 A1* | 1/2002 | Sander ........................ 141/59 |
| 2005/0112541 A1* | 5/2005 | Durack et al. ................ 435/2 |

(Continued)

FOREIGN PATENT DOCUMENTS

| JP | 57-196155 A | 2/1982 |
| JP | 05-293391 A | 11/1993 |

(Continued)

OTHER PUBLICATIONS

Supplementary European Search Report EP 11 86 1977 dated Dec. 22, 2014.

(Continued)

*Primary Examiner* — Jill Warden
*Assistant Examiner* — Brittany Fisher
(74) *Attorney, Agent, or Firm* — McDermott Will & Emery LLP

(57) ABSTRACT

A dispensing device includes: a syringe including a nozzle; a first pump configured to generate a pressure to discharge a liquid in the syringe through the nozzle; and a control unit configured to, when discharging the liquid in the syringe, discharge a part of the liquid in the syringe with the pressure generated by the first pump and then cause the liquid in the syringe to run out under its own weight.

9 Claims, 15 Drawing Sheets

(56) References Cited

U.S. PATENT DOCUMENTS

2009/0010809 A1  1/2009  Hadjis et al.
2009/0180930 A1* 7/2009  Aoki et al. ................. 422/63

FOREIGN PATENT DOCUMENTS

| | | |
|---|---|---|
| JP | 11-244757 A | 9/1999 |
| JP | 2004-141857 A | 5/2004 |
| JP | 2006-158335 A | 6/2006 |
| JP | 2006-184009 A | 7/2006 |
| JP | 2009-291103 A | 12/2009 |
| WO | 2004/062805 A1 | 7/2004 |

OTHER PUBLICATIONS

International Search Report in PCT/JP2011/079826 dated Apr. 10, 2012 with English translation.

* cited by examiner

DISPENSING DEVICE AND DISPENSING SYSTEM

CROSS-REFERENCE TO RELATED APPLICATIONS

This is a continuation application of International Patent Application No. PCT/JP2011/079826 filed Dec. 22, 2011, which claims the benefit of priority to Japanese Patent Application Nos. 2011-070595 and 2011-070596 both filed Mar. 28, 2011. The full contents of the International Patent Application are incorporated herein by reference.

BACKGROUND OF THE INVENTION

1. Field of the Invention

The present disclosure relates to a dispensing device and a dispensing system.

2. Description of the Related Art

A dispensing device (dispenser) configured to discharge a liquid from a nozzle using a syringe, and the like, has been utilized for various purposes.

For example, Japanese Patent Application Laid-open Publication No. 2009-291103 discloses an automatic cell-culture apparatus including a dispensing device (pipette device) which is used in a pipetting operation with respect to a culture container. Further, Japanese Patent Application Laid-open Publication No. 2004-141857 discloses a dispensing device which can be used for a printer head of an ink-jet printer.

The dispensing device as described above discharges a liquid from the nozzle by applying a pressure to the liquid. For example, a common ink-jet printer discharges an ink drop by applying a pressure to the ink drop using a piezo element (piezoelectric element) or using air bubbles generated by heating. Further, for example, a continuous type (continuous discharging type) ink-jet printer or a dispensing device using a syringe is capable of generating a pressure using a pump and discharging a liquid.

However, in the case of dispensing a liquid using a pump, a liquid phase and a gas phase are easily mixed at the tip of the nozzle at the start and/or end of dispensing, which may cause a splatter and/or a bubble. If a splatter is generated, the liquid may splatter over something other than a liquid dispensing target, thereby contaminating the surroundings. Further, also in the case where a bubble is generated, the bubble may burst into splatters or the bubble at the tip of the nozzle may drip when the syringe is moved, thereby contaminating the surroundings.

In particular, such a dispensing device as to be used for a cell culture apparatus does not discharge a solution continuously, which is different from the case with a continuous type ink-jet printer, and thus, the splatter and/or bubble may be generated every start and/or end of dispensing. Therefore, when a solution is discharged using a pump, the solution may splatter over the outside of a dish (culture dish) or drip off the dish, which may result in contamination.

SUMMARY OF THE INVENTION

A dispensing device according to an aspect of the present disclosure includes: a syringe including a nozzle; a first pump configured to generate pressure for discharging liquid in the syringe through the nozzle; and a control unit configured to discharge the liquid in the syringe by discharging a part of the liquid in the syringe using pressure generated by the first pump and then causing the liquid in the syringe to flow out due to its own weight.

Other features of the present disclosure will become apparent from descriptions of the present specification and of the accompanying drawings.

BRIEF DESCRIPTION OF THE DRAWINGS

For more thorough understanding of the present disclosure and advantages thereof, the following description should be read in conjunction with the accompanying drawings, in which.

DETAILED DESCRIPTION OF THE INVENTION

At least the following details will become apparent from descriptions of the present specification and of the accompanying drawings.

===Configuration of Dispensing System and Dispensing Apparatus===

A configuration of a dispensing system and a dispensing device according to an embodiment of the present disclosure will be hereinafter described with reference to FIG. 1 and FIG. 2.

Figure 2:
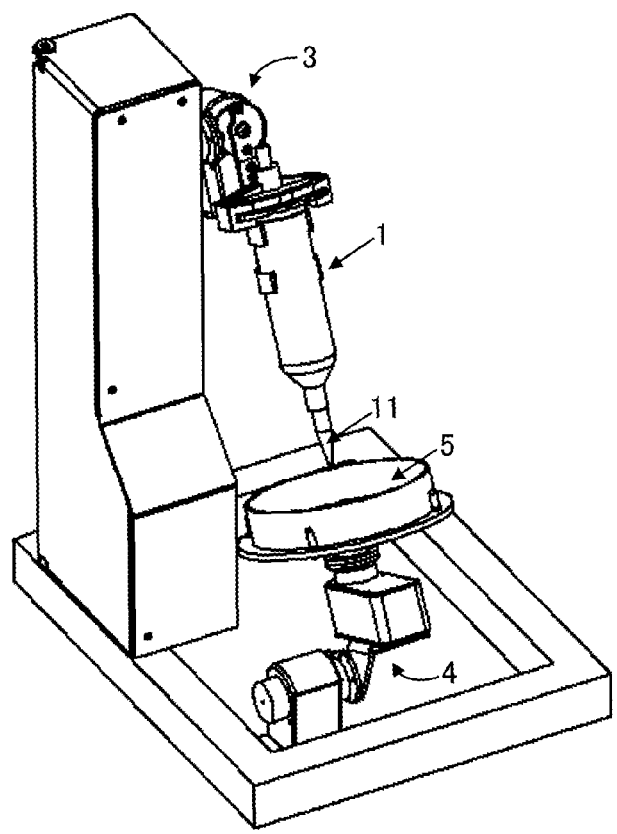
FIG. 2 is an exemplary perspective view illustrating an application example of a dispensing system including a dispensing device according to an embodiment of the present disclosure.

FIG. 2 depicts a configuration of a cell culture apparatus as an example of the application of the dispensing system including the dispensing device according to an embodiment of the present disclosure. The dispensing system (cell culture apparatus) illustrated in FIG. 2 includes: a syringe 1 configured to dispense a liquid (dispensing solution such as a culture medium); and a dish 5, configured to contain a culture medium, as a target to which the liquid is to be dispensed, and further includes a syringe drive portion 3 and a dish drive portion 4 configured to drive the syringe 1 and the dish 5, respectively. The syringe 1 includes a nozzle 11.

Note that the syringe drive portion 3 is capable of controlling the position and posture of the nozzle 11 by controlling the position and posture of the syringe 1, and the dish drive portion 4 is capable of controlling the position, posture, and further rotation, for example, of the dish 5. Under the control of the syringe drive portion 3 and the dish drive portion 4, the relative position between the syringe 1 (nozzle 11) and the dispensing target can be controlled, and the syringe 1 (nozzle 11) can be relatively moved to the position at which the liquid is to be dispensed to the target. The syringe drive portion 3 and the dish drive portion 4 are hereinafter collectively referred to as a drive portion.

Figure 1:
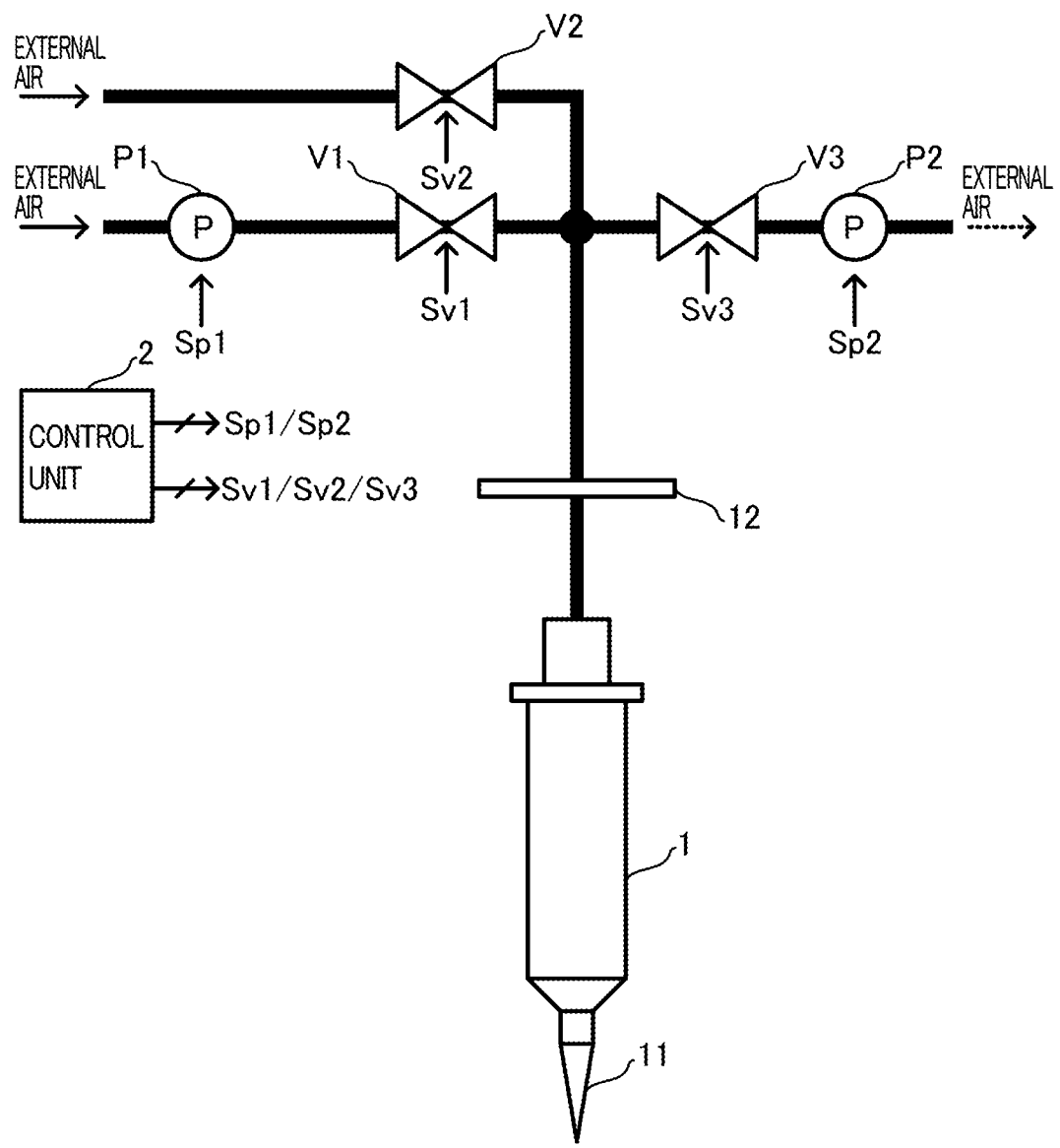
FIG. 1 is an exemplary view of a block diagram illustrating a configuration of a dispensing device according to an embodiment of the present disclosure.

The dispensing device depicted in FIG. 1 includes a control unit 2, a filter 12, pumps P1 and P2, and valves V1 to V3, in addition to the syringe 1. The control unit 2 is configured to output control signals Sp1, Sp2, and Sv1 to Sv3 for controlling the pumps and the valves, respectively.

The (first) pump P1 is a discharge pump configured to take in external air to the syringe 1 and generate a pressure to discharge the liquid in the syringe 1 through the nozzle 11. The (second) pump P2 is a suction pump configured to discharge the gas (air) in the syringe 1 and generate a pressure (negative pressure) and draw the liquid into the syringe 1 through the nozzle 11.

The (first) valve V1 is connected so as to open/close a (first) flow path between the syringe 1 and the pump P1. The (second) valve V2 is connected so as to open/close a (second) flow path between the syringe 1 and external air. The (third) valve V3 is connected so as to open/close a (third) flow path between the syringe 1 and the pump P2. Note that, for example, a solenoid valve and a motor-operated pinch valve, which can be controlled by a control signal, can be used as the valves.

The first to the third flow paths join and branch at one point, and the filter 12 such as a membrane filter is inserted into a flow path between the converging-and-diverging point and the syringe 1, in order to prevent contamination of the liquid in the syringe 1 which would be caused by unwanted bacteria mixing therewith. Further, flow paths between external air and the pumps P1, P2 as well as the valve V2 may converge and diverge as appropriate.

===First Control of Dispensing Apparatus===

The operation of the dispensing device according to an embodiment of the present disclosure is hereinafter described with reference to FIG. 3 to FIG. 8.

Figure 3:
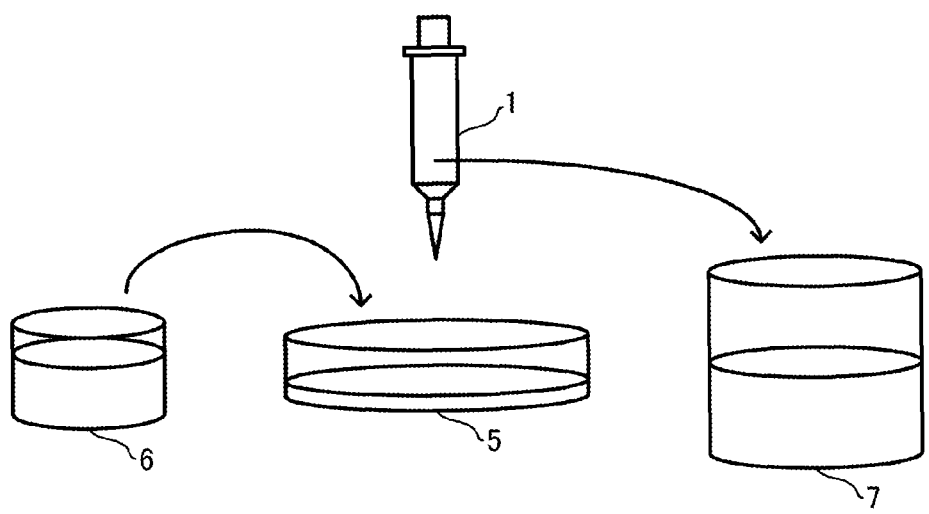
FIG. 3 is an exemplary view of a diagram illustrating one example of operations of filling and dispensing a liquid using a dispensing device according to an embodiment of the present disclosure.
Figure 4:
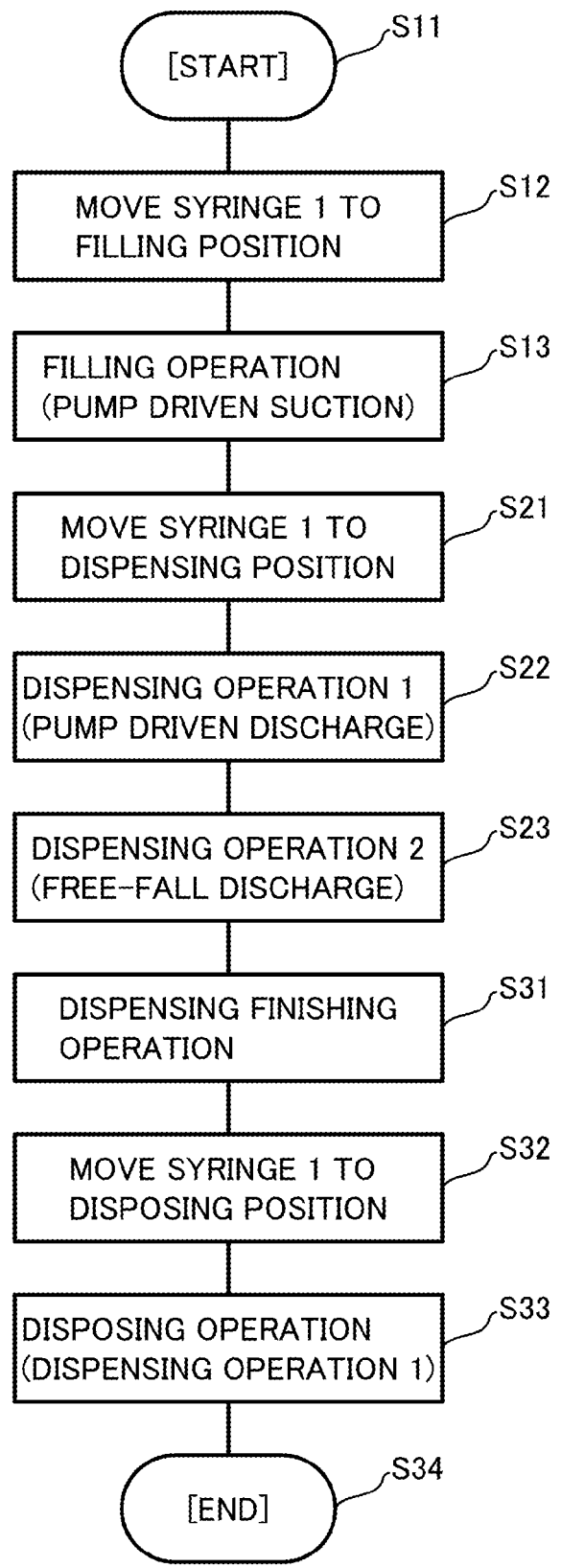
FIG. 4 is an exemplary flowchart explaining a flow of control of a dispensing device according to an embodiment of the present disclosure.

FIG. 3 illustrates one example of a series of operations of filling and dispensing the liquid using the dispensing device according to an embodiment of the present disclosure. FIG. 4 illustrates the control flow of the dispensing device when the filling and dispensing operations are performed. In FIG. 3, the dispensing device performs a series of filling/dispensing operations including drawing the liquid such as a medium solution stored in a reservoir 6 into the syringe 1 (filling operation), discharging the liquid in the syringe 1 to the dish 5 (dispensing operation), and thereafter discharging the liquid, bubbles, and the like, remaining in the syringe 1 to a waste liquid tank 7 (disposing operation).

The dispensing device can draw in the liquid from the dish 5 (filling operation) and discharge the liquid into the reservoir 6 (dispensing operation), can draw in the liquid from the dish 5 (filling operation) and discharge the liquid into the dish 5 (dispensing operation), or can draw in the liquid from the reservoir 6 (filling operation) and discharge the liquid into the reservoir 6 (dispensing operation). Further, the dispensing device can draw in the liquid from the reservoir 6 (filling operation) and discharge the liquid into the waste liquid tank 7 (disposing operation). Hereinafter, in any case, positions to which the syringe 1 (nozzle 11) is to be moved to perform the filling operation, the dispensing operation, and the disposing operation are referred to as a filling position, a dispensing position, and a disposing position, respectively.

Figure 5:
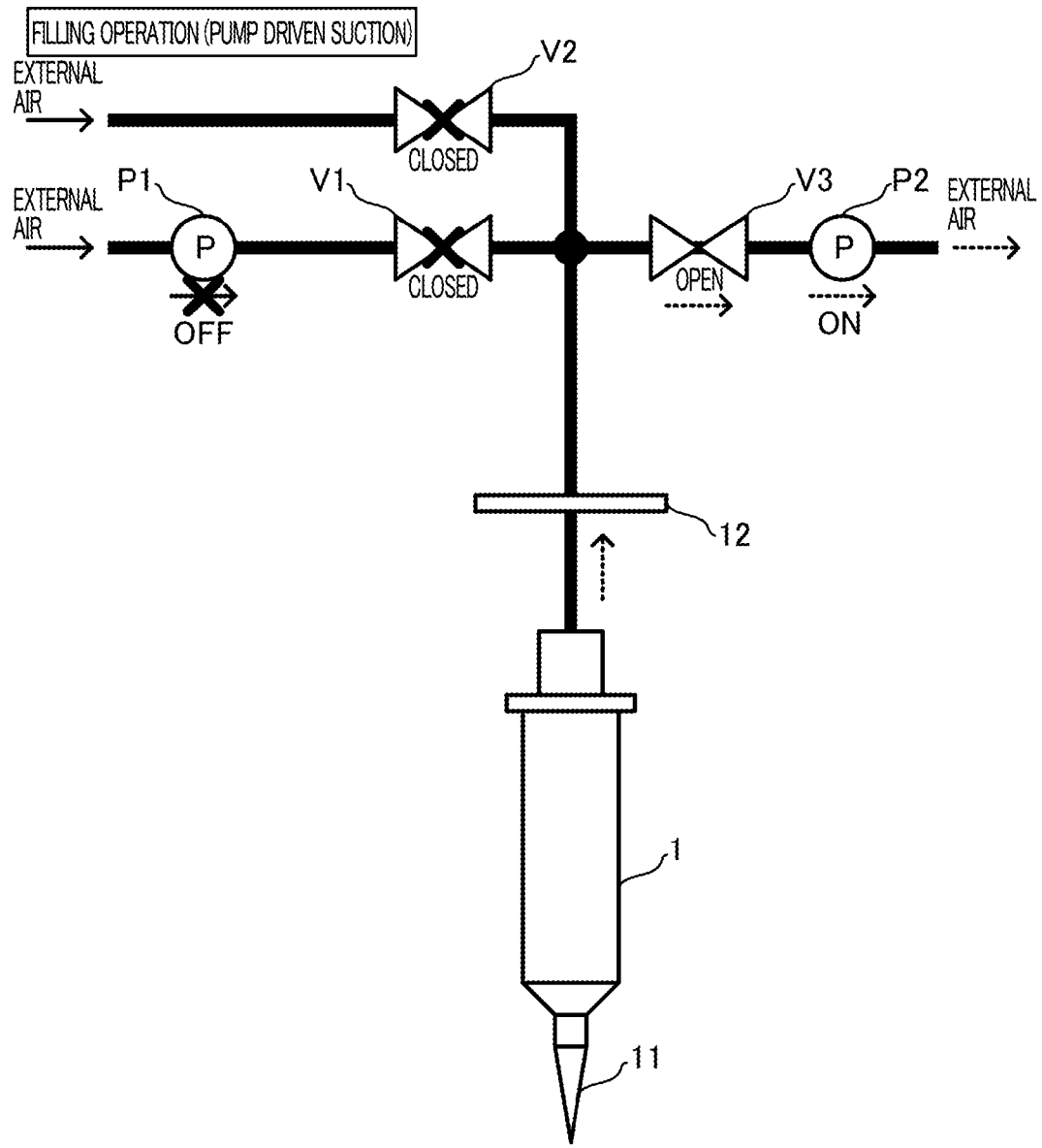
FIG. 5 is an exemplary view of a block diagram illustrating a state of valves and pumps in a filling operation.

In FIG. 4, when the dispensing device starts a series of filling and dispensing operations (S11), first, the syringe 1 is moved to the filling position (reservoir 6 in FIG. 3) under the control of the drive portion (S12), and the filling operation is performed (S13). In the filling operation, as depicted in FIG. 5, under the control of the control unit 2, the pump P1 is stopped, the pump P2 is driven with the valves V1 and V2 closed, and the valve 3 is opened, thereby drawing the liquid into the syringe 1 using the pressure (negative pressure) generated by the pump P2 (pump driven suction).

Next, in the dispensing device, the syringe 1 is moved to the dispensing position (dish 5 in FIG. 3) under the control of the drive portion (S21), and the dispensing operation is performed (S22 and S23). The dispensing operation according to an embodiment of the present disclosure includes: the dispensing operation 1 (S22) which is performed from the start of dispensing; and the dispensing operation 2 (S23) which is performed subsequent to the dispensing operation 1.

Figure 6:
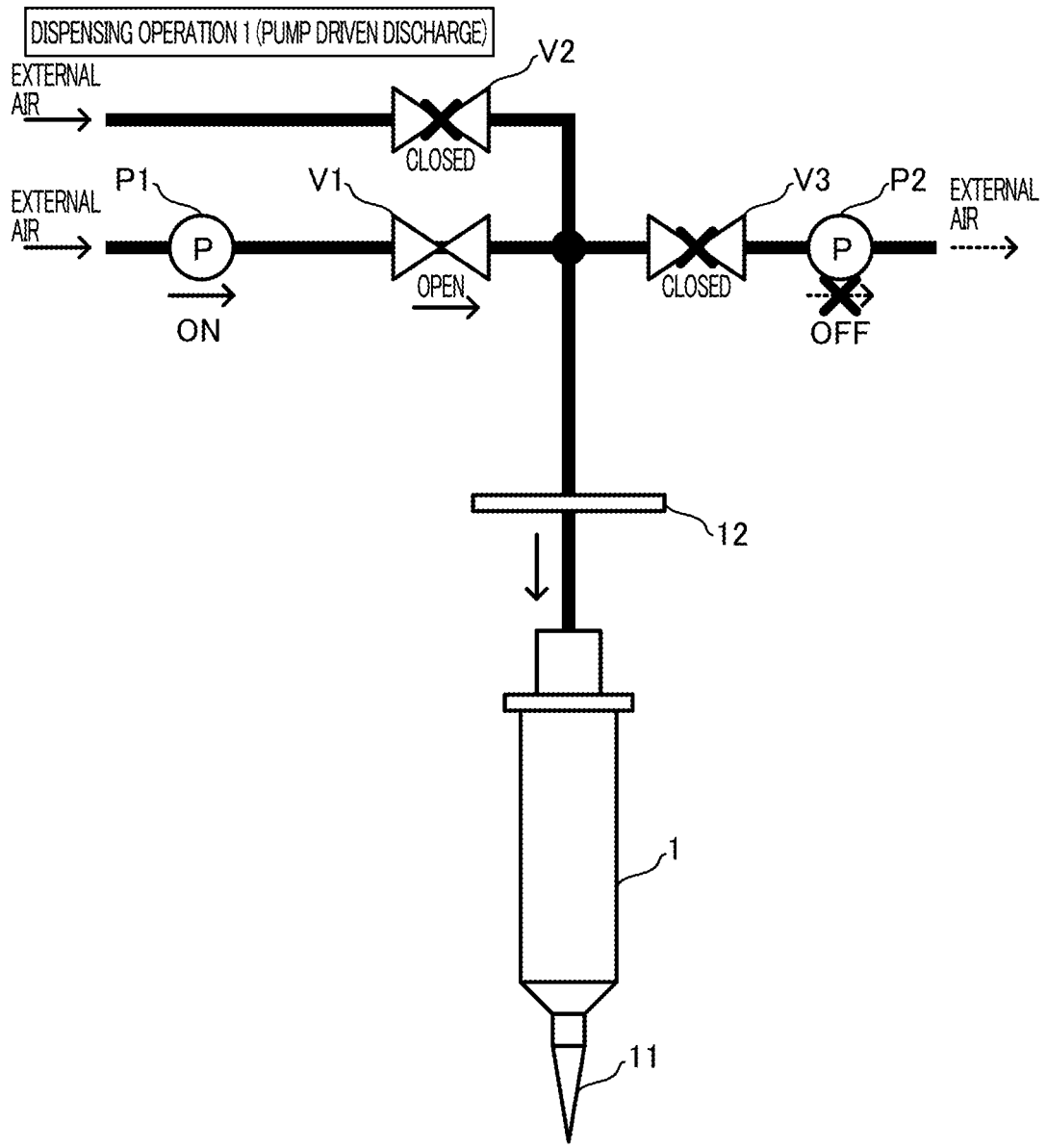
FIG. 6 is an exemplary view of a block diagram illustrating a state of valves and pumps in a dispensing operation 1.
Figure 7:
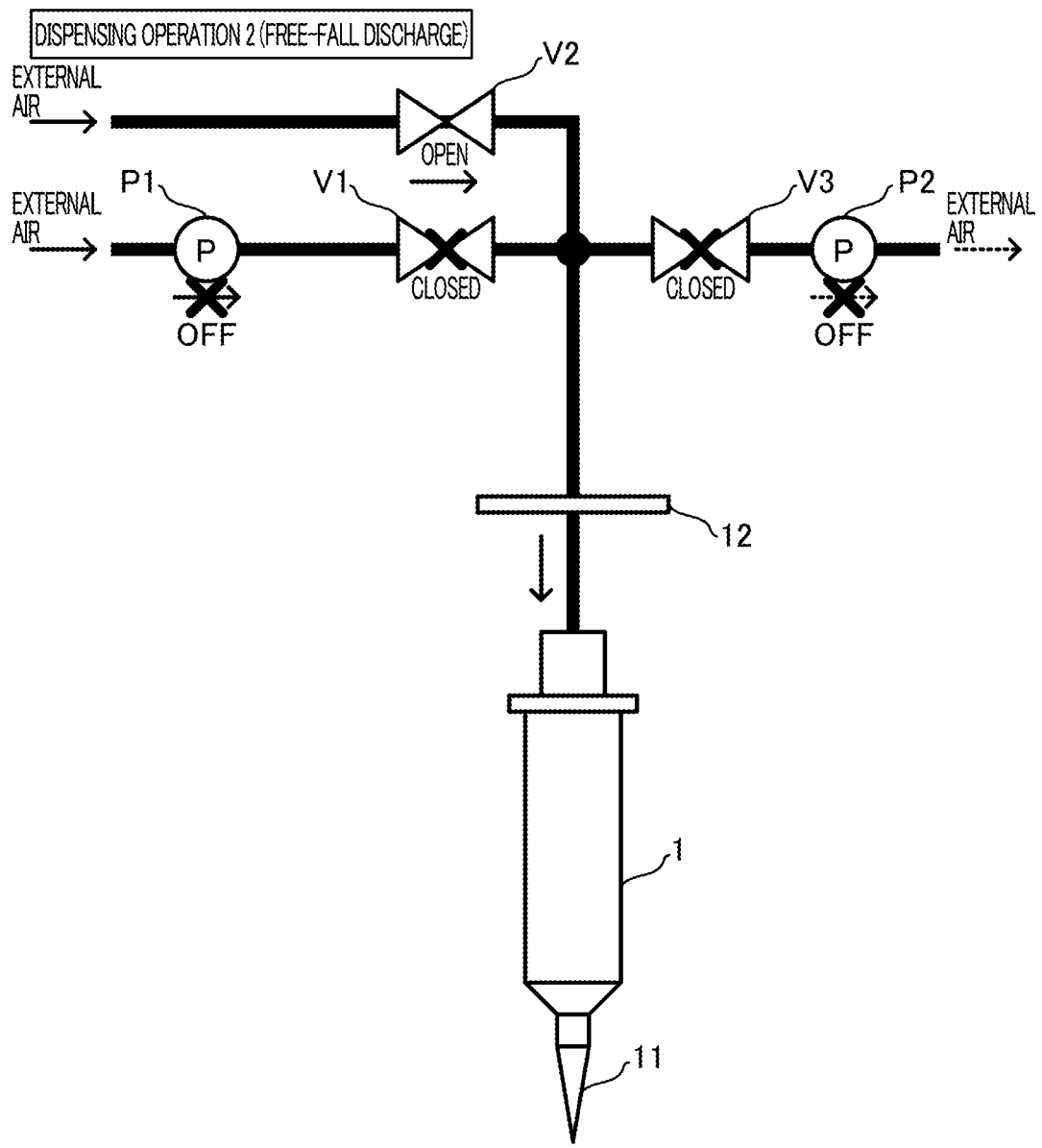
FIG. 7 is an exemplary view of a block diagram illustrating a state of valves and pumps in a dispensing operation 2.

In the dispensing operation 1, as depicted in FIG. 6, the pump P2 is stopped and the valve V3 is closed with the valve V2 closed, and further the pump P1 is driven and the valve V1 is opened, under the control of the control unit 2, thereby discharging a part of the liquid in the syringe 1 using the pressure generated by the pump P1 (pump driven discharge). In the dispensing operation 2, as depicted in FIG. 7, the pump P2 is stopped, the pump P1 is stopped as well as the valve V1 is closed with the valve V3 closed, and the valve V2 is opened, under the control of the control unit 2, thereby causing the liquid in the syringe 1 to run out under its own weight, that is, free-fall. In an embodiment of the present disclosure, flowing out of the liquid in such a free-fall is referred to as free-fall discharge.

As such, the dispensing device according to an embodiment of the present disclosure performs the dispensing operation 1 from the start of dispensing, and performs the dispensing operation 2 after the dispensing operation 1. Thus, after quickly performing dispensing by the pump driven discharge, only the liquid can be gradually dispensed in the free-fall discharge, thereby being able to suppress generation of droplets and bubbles at the end of dispensing, and prevent the contamination of something other than the liquid dispensing target.

Figure 8:
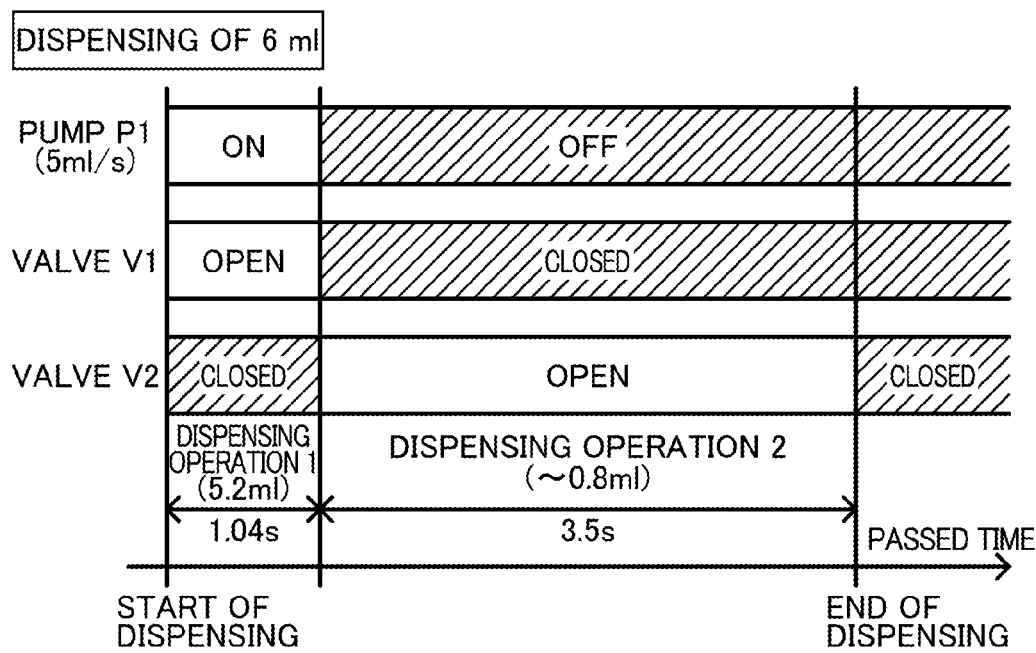
FIG. 8 is an exemplary view of a diagram illustrating an example of operation times of dispensing operations 1 and 2 when dispensing 6 ml of a liquid.

Here, FIG. 8 depicts, by way of example, each operation time of the dispensing operations 1 and 2 when dispensing 6 ml of a liquid using the pump 1, which is configured to discharge a liquid at 5 ml/s. In FIG. 8, a large part (a little under 90%) of the liquid in the syringe 1 is discharged from the nozzle 11 by performing the dispensing operation 1 for 1.04 seconds from the start of dispensing. Subsequently, the dispensing operation 2 is performed for 3.5 seconds, thereby causing substantially all of the remaining liquid (a little over 10%) in the syringe 1 to run out from the nozzle 11.

Note that, at this time in the dispensing operation 2, a very small amount of the liquid can remain in the syringe 1 and/or the nozzle 11 by the surface tension of the liquid. Therefore, the bubbles, which are generated when the final liquid drops are forcibly discharged by the pump driven discharge, and the droplets, which are generated by the burst of the bubbles, can be suppressed. Further, the inner diameter of the discharge port (tip) of the nozzle 11 is set in consideration of the surface tension of the liquid to be dispensed and the like, and in an embodiment of the present disclosure, the inner diameter is assumed to be approximately 0.25 mm to 5.0 mm, by way of example.

Further, in an embodiment of the present disclosure, the amount of the liquid to be discharged by the dispensing operation 1 is set in consideration of an error in fluid delivery volume in the pump. For example, when an error in the fluid delivery volume is within ±10%, setting is made such that a little under 90% of the whole discharge amount is discharged by the dispensing operation 1, so that the amount corresponding to an error in the fluid delivery volume remains in the syringe 1 without the whole amount being discharged by the pump driven discharge. Thus, generation of bubbles and droplets is avoided, which would be generated if the pump driven discharge where performed to the end.

Next, the dispensing device performs a dispensing finishing operation (S31). In the dispensing finishing operation, in order to prevent droplets and bubbles from dropping from the nozzle 11 which is caused by the movement of the syringe 1, for example, the tip of the nozzle 11 is brought into contact with the liquid surface or the end face of the dish 5 under the control of the drive portion, thereby removing droplets and bubbles at the tip of the nozzle 11.

Finally, the dispensing device moves the syringe 1 to the liquid disposing position (waste liquid tank 7 in FIG. 3) under the control of the drive portion (S32), the disposing operation is performed (S33), and a series of the filling and dispensing operations ends (S34). In the disposing operation, similarly to the dispensing operation 1, the pump driven discharge is performed under the control of the control unit 2, so that the liquid, bubbles, etc., remaining in the syringe 1 are discharged into the waste liquid tank 7, using the pressure generated by the pump P1 (pump driven discharge). Note that it is desirable to take measures so as not to contaminate the surroundings even if the pump driven discharge is performed, such that the disposing operation is performed, for example, with the nozzle 11 being deeply inserted into the waste liquid tank 7 having a sufficient depth and with the tip of the nozzle 11 being brought into contact with the inner wall of the waste liquid tank 7.

===Another Configuration Example of Dispensing Apparatus===

Figure 9:
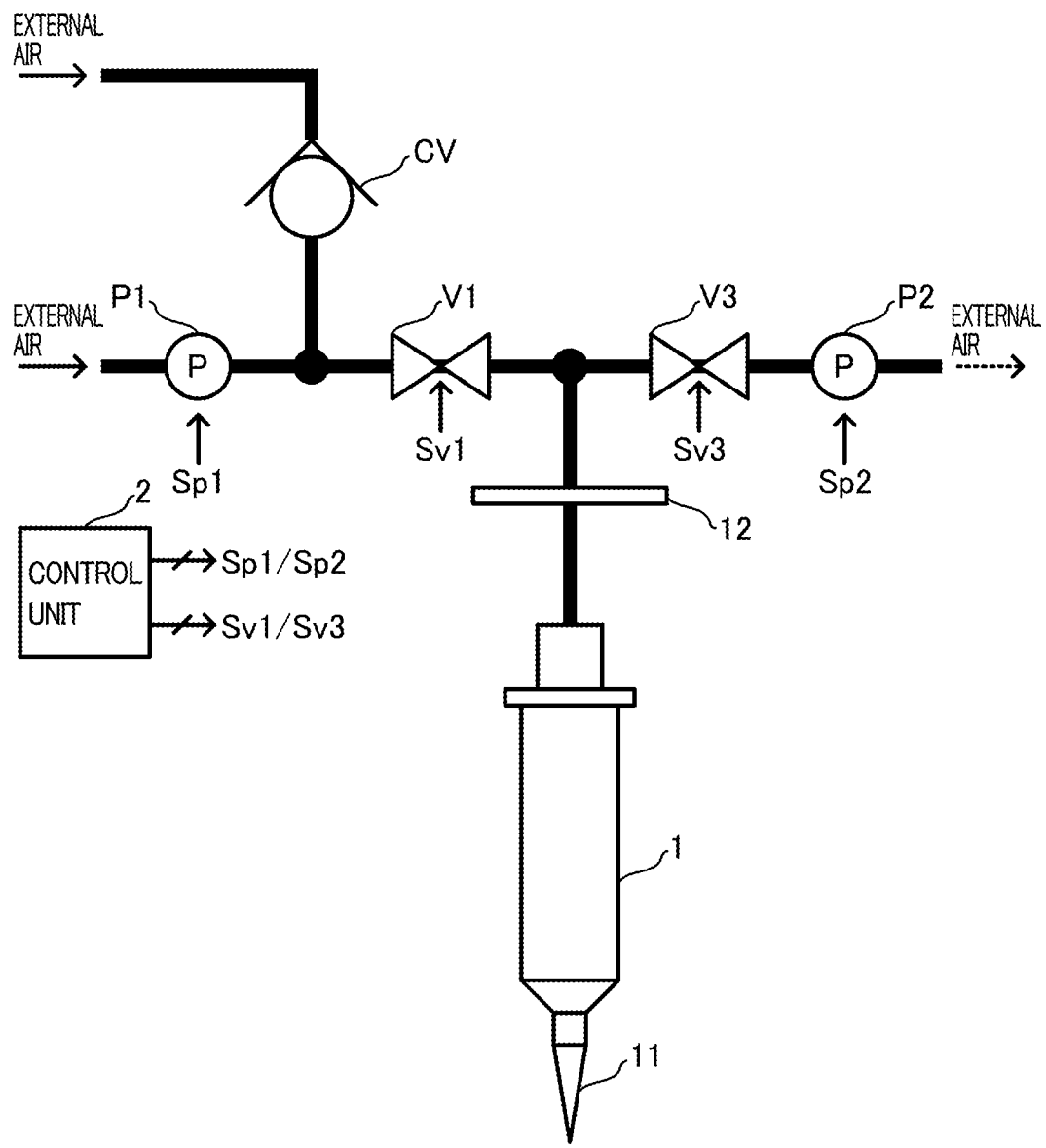
FIG. 9 is an exemplary view of a block diagram illustrating another structure example of a dispensing device.

In an embodiment described above, the control unit 2 of the dispensing device outputs control signals for controlling the two pumps P1 and P2 and the three valves V1 to V3, but it is not limited thereto. For example, as depicted in FIG. 9, a check valve CV which does not require the control of the control unit 2 may be used as the second valve in place of the valve V2. In the dispensing device, the check valve CV is connected so as to open/close the (second) flow path between external air and the flow path between the pump P1 and the valve V1, and allow external air to flow in but prevent air from flowing out to external air.

Figure 10:
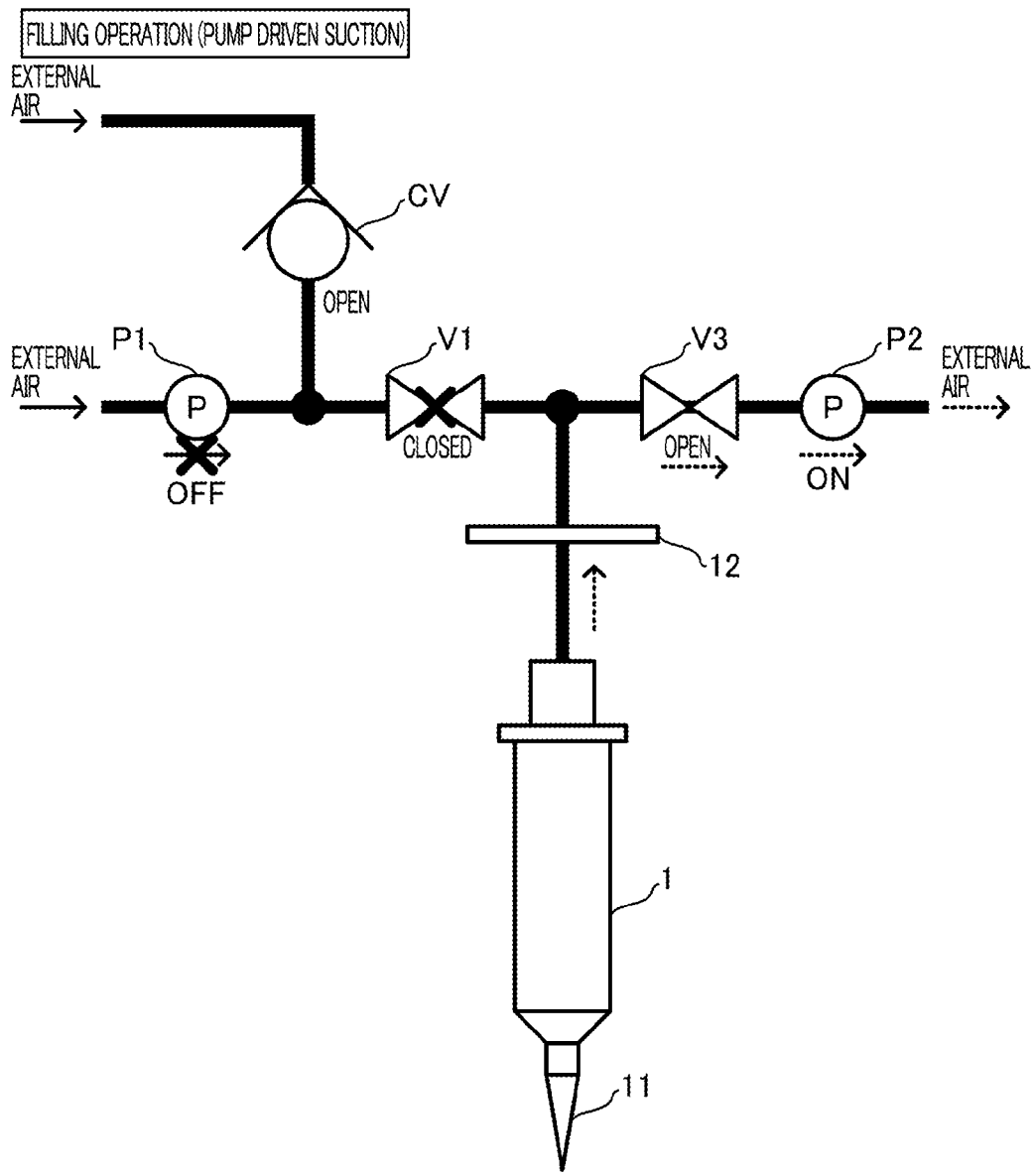
FIG. 10 is an exemplary view of a block diagram illustrating a state of valves and pumps in a filling operation in a dispensing device illustrated in FIG. 9.

When the check valve CV is used, in the filling operation, the pump P1 is stopped, and the pump P2 is driven as well as the valve V3 is opened with the valve V1 closed, under the control of the control unit 2, as depicted in FIG. 10, thereby being able to perform the pump driven suction.

Figure 11:
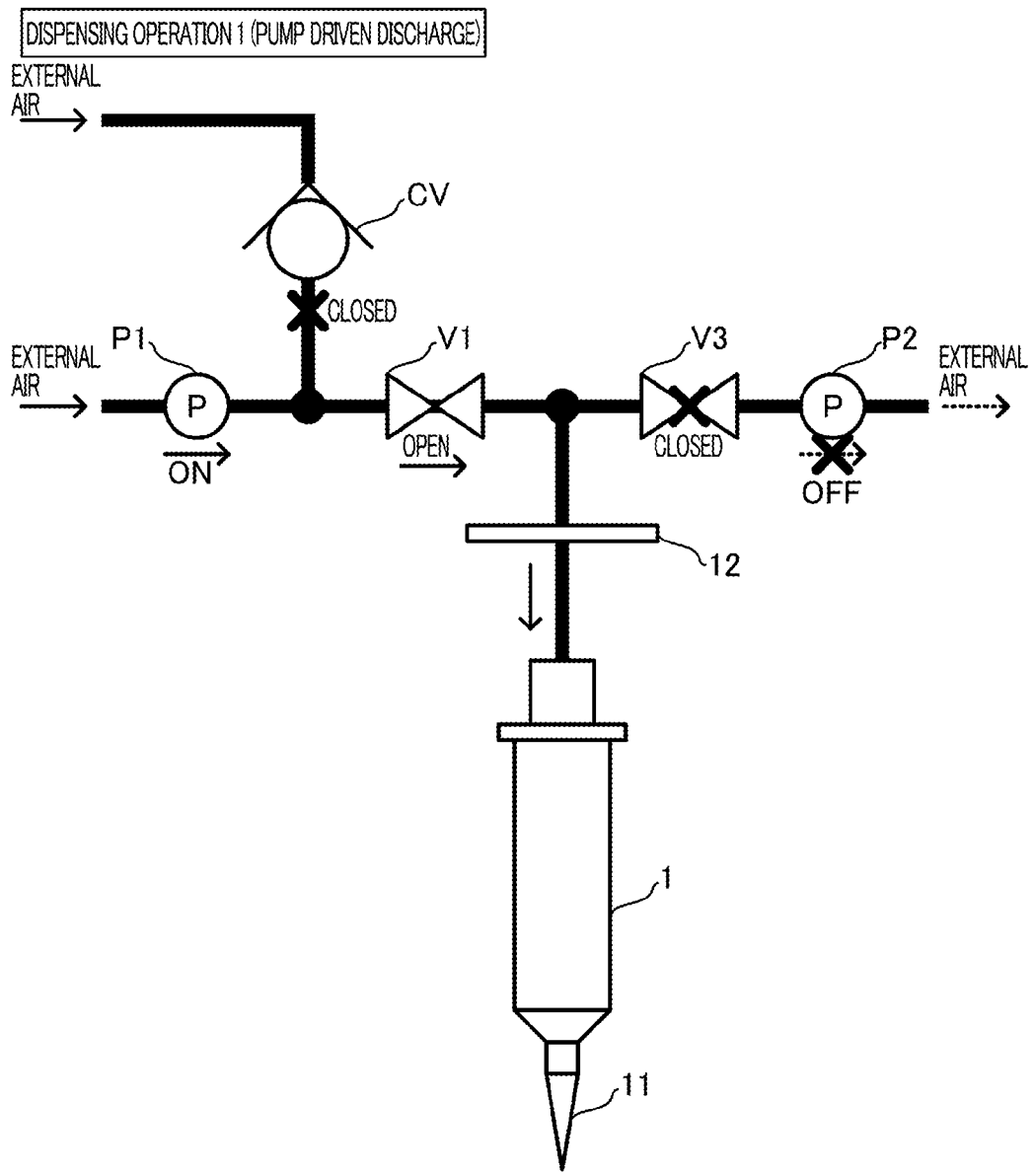
FIG. 11 is an exemplary view of a block diagram illustrating a state of valves and pumps in a dispensing operation 1 in a dispensing device illustrated in FIG. 9.

In the dispensing operation 1, as depicted in FIG. 11, under the control of the control unit 2, the pump P2 is stopped and the valve V3 is closed, and further the pump P1 is driven and the valve V1 is opened. In this case, since the check valve CV is closed by the pressure generated by the pump P1, the pump driven discharge can be performed.

Figure 12:
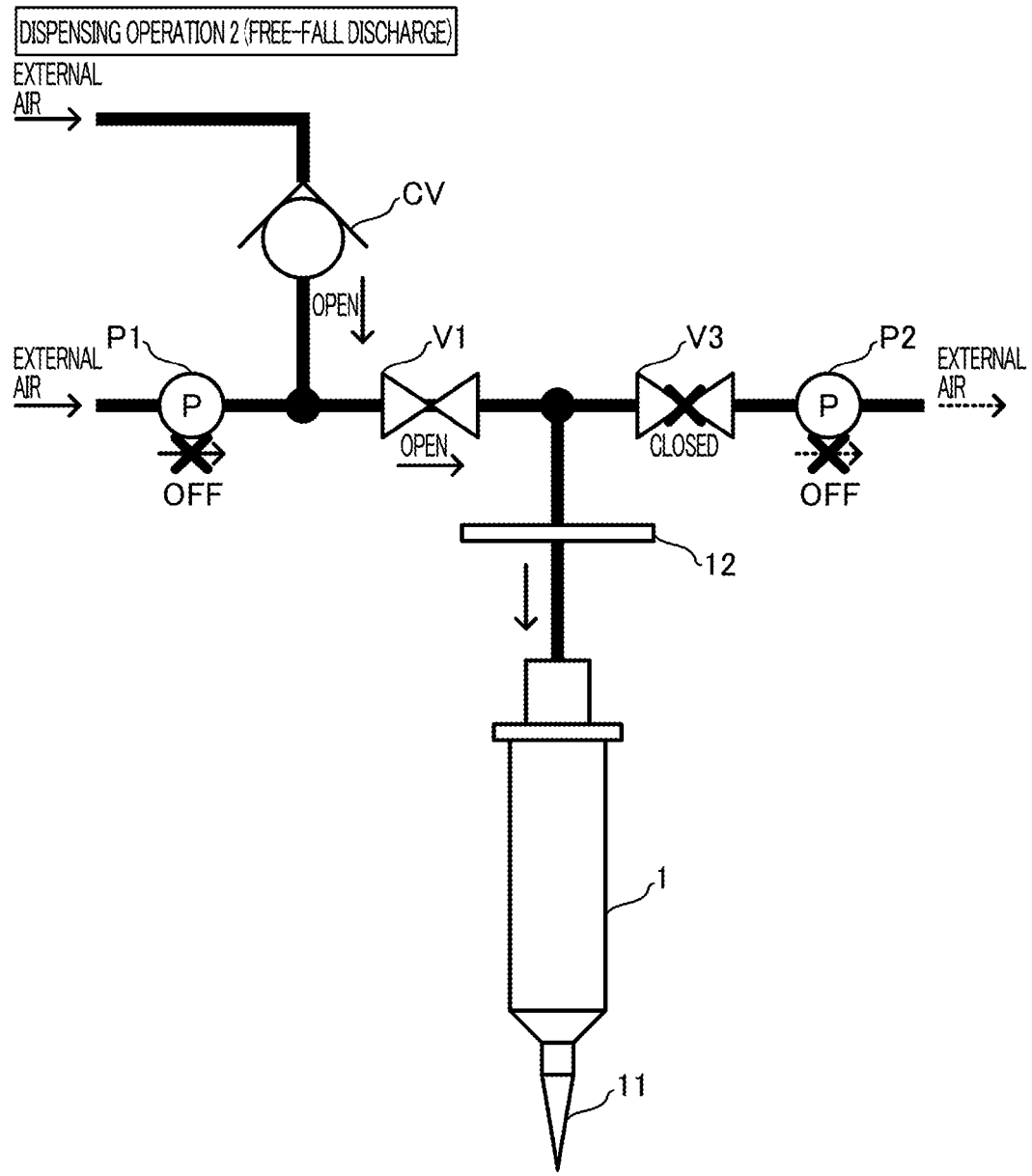
FIG. 12 is an exemplary view of a block diagram illustrating a state of valves and pumps in a dispensing operation 2 in a dispensing device illustrated in FIG. 9.

Further, in the dispensing operation 2, as depicted in FIG. 12, the pump P2 is stopped, the valve V3 is closed, and the pump P1 is stopped with the valve V1 open, under the control of the control unit 2. In this case, since the check valve CV is opened by the pressure (negative pressure) applied under its own weight of the liquid in the syringe 1, external air can be flown into the syringe 1 through the check valve CV and the valve V1, thereby being able to perform the free-fall discharge.

As such, in the dispensing device depicted in FIG. 9, the control unit 2 only has to output the control signals for controlling the two pumps P1 and P2 and the two valves V1 and V3, thereby being able to reduce the control signals. However, in the dispensing device, the pressure for opening the check valve CV is only the pressure (negative pressure) under its own weight of the liquid in the syringe 1, and thus there exists a possibility that the check valve CV is not sufficiently opened depending on the condition such as a shape of the nozzle 11 and the viscosity of the liquid. Whereas, in the dispensing device depicted in FIG. 1, the free-fall discharge can be reliably performed by controlling the valve V2.

As has been described, in the dispensing device depicted in FIG. 1 and FIG. 9, the dispensing operation 1 is performed from the start of dispensing, and the dispensing operation 2 is performed after the dispensing operation 1, thereby being able to perform quick dispensing by the pump driven discharge, and thereafter gradually dispense only the liquid in the free-fall discharge. Thus, splatters and bubbles are prevented from being generated at the end of dispensing, thereby being able to prevent contamination of something other than the liquid dispensing target.

Further, in the dispensing device depicted in FIG. 1, the control unit 2 controls the valve V1 for opening/closing the (first) flow path between the syringe 1 and the pump P1 for discharge and the valve V2 for opening/closing the (second) flow path between the syringe 1 and external air, thereby being able to reliably perform the free-fall discharge after performing the pump driven discharge.

===Second Control of Dispensing Apparatus===

Next, a description will be give of second control of the dispensing device according to an embodiment of the present disclosure.

Figure 15:
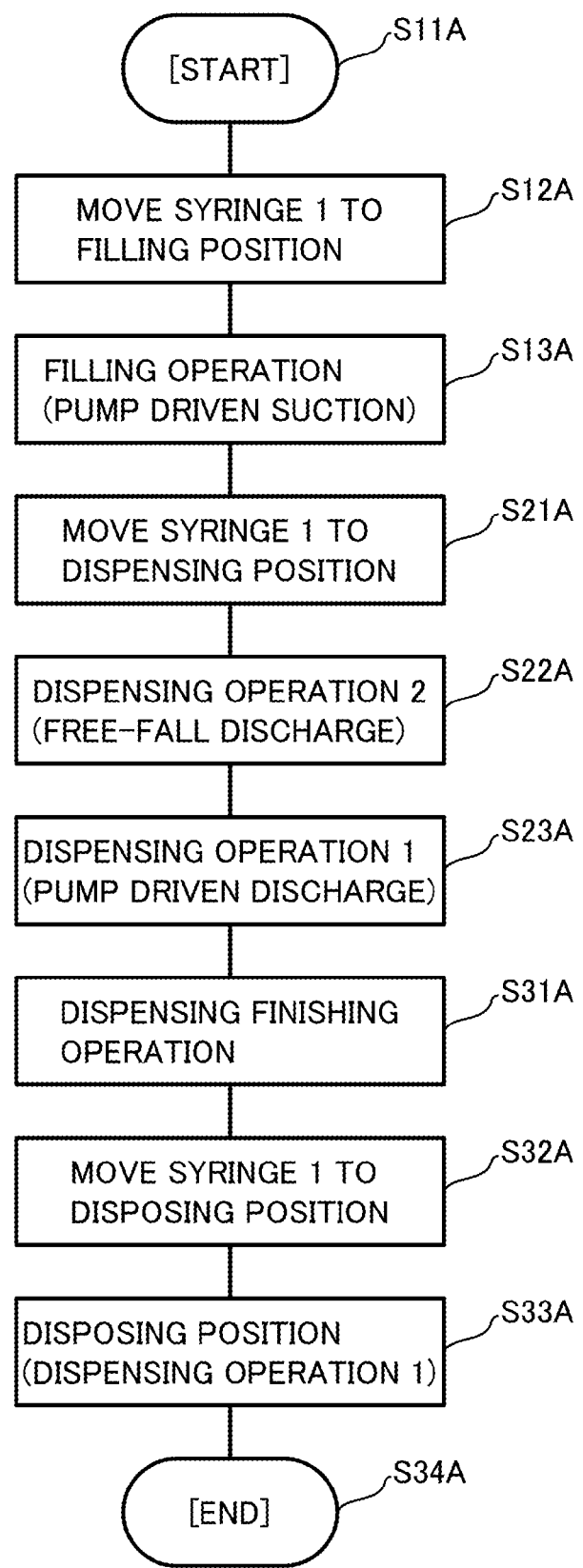
FIG. 15 is an exemplary flowchart explaining control of a dispensing device according to an embodiment of the present disclosure.

FIG. 15 depicts a flow of the second control of the dispensing device when the filling and dispensing operations are performed.

In FIG. 15, when the dispensing device starts a series of the filling and dispensing operations (S11A), firstly, the syringe 1 is moved to the filling position (reservoir 6 in FIG. 3) under the control of the drive portion (S12A), and the filling operation is performed (S13A). In the filling operation, as depicted in FIG. 5, the pump P1 is stopped, and the pump P2 is driven as well as the valve V3 is opened with the valves V1 and V2 closed, under the control of the control unit 2, thereby drawing the liquid into the syringe 1 by the pressure (negative pressure) generated by the pump P2 (pump driven suction).

Next, in the dispensing device, the syringe 1 is moved to the dispensing position (dish 5 in FIG. 3) under the control of the drive portion (S21A) and the dispensing operation is performed (S22A and S23A). The dispensing operation according to an embodiment of the present disclosure includes the dispensing operation 2 (S22A), which is performed at the start of dispensing, and the dispensing operation 1 (S23A), which is performed subsequent to the dispensing operation 2.

In the dispensing operation 2, as depicted in FIG. 7, the pump P1 is stopped, the pump P2 is stopped as well as the valve V3 is closed with the valve V1 closed, and the valve V2 is opened, under the control of the control unit 2, thereby causing a part of the liquid in the syringe 1 to run out under its own weight, that is, free-fall. In an embodiment of the present disclosure, flowing out of the liquid in such a free-fall is referred to as free-fall discharge. Further, in the dispensing operation 1, as depicted in FIG. 6, the pump P2 is stopped, the valve V2 is closed and the pump P1 is driven as well as the valve V1 is opened with the valve V3 closed, under the control of the control unit 2, thereby discharging the liquid in the syringe 1 using the pressure generated by the pump P1 (pump driven discharge).

As such, the dispensing device according to an embodiment of the present disclosure performs the dispensing operation 2 at the start of dispensing, and then performs the dispensing operation 1 after the dispensing operation 2. Therefore, it becomes possible to gradually start dispensing in a free-fall discharge and perform the pump driven discharge after removing the gas phase at the tip of the nozzle 11, thereby being able to suppress generation of splatters and bubbles at the start of dispensing, and prevent contamination of something other than the liquid dispensing target.

Figure 16:
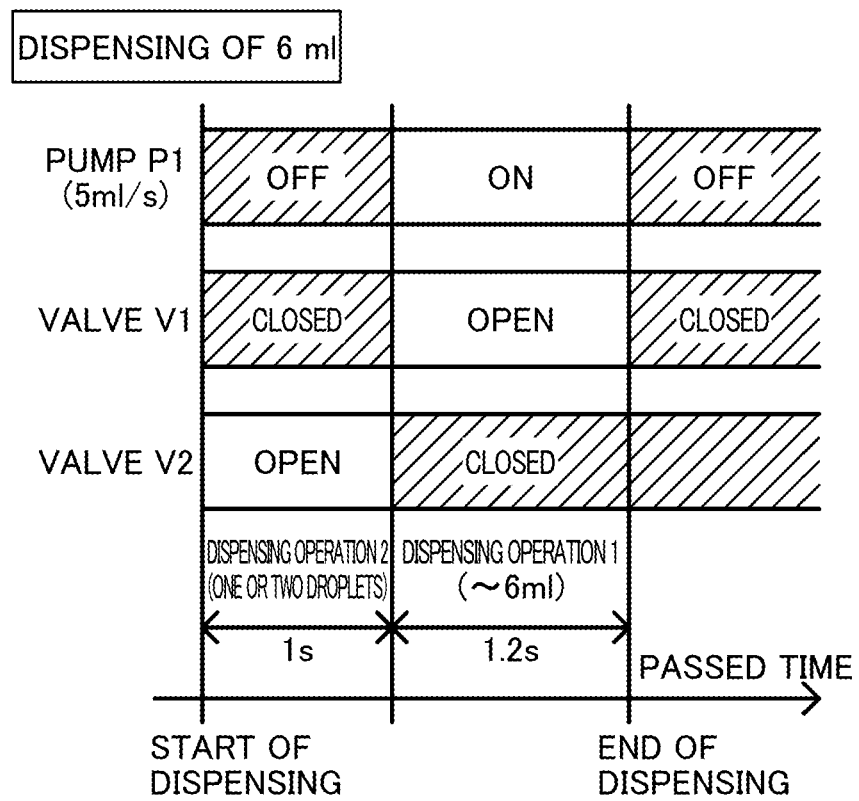
FIG. 16 is an exemplary view of a diagram illustrating an example of operation times of dispensing operations 1 and 2 when dispensing 6 ml of a liquid.

Here, FIG. 16 depicts each operation time of the dispensing operations 1 and 2 when dispensing 6 ml of the liquid using the pump P1, which is configured to discharge the liquid at 5 ml/s, by way of example. In FIG. 16, when starting dispensing, a small amount (about one drop or two) of the liquid in the syringe 1 runs out from the nozzle 11 by performing the dispensing operation 2 for one second. Further, substantially all of the liquid in the syringe 1 is discharged from the nozzle 11, by subsequently performing the dispensing operation 1 for 1.2 seconds. Note that, although the dispensing operation 1 is performed for 1.2 seconds at 5 ml/s, a small amount of liquid and/or bubbles may remain in the syringe 1 in actuality.

Next, the dispensing device performs the dispensing finishing operation (S31A). In the dispensing finishing operation, in order to prevent a droplet and a bubble from dripping from the nozzle 11 due to the movement of the syringe 1, for example, the tip of the nozzle 11 is brought into contact with the liquid surface or the end surface of the dish 5 under the control of the drive portion, thereby removing a droplet and a bubble at the tip of the nozzle 11.

Finally, the dispensing device moves the syringe 1 to the liquid disposing position (waste liquid tank 7 in FIG. 3) under the control of the drive portion (S32A), performs an operation of disposing the waste liquid (S33A), and finishes a series of the filling and dispensing operations (S34A).

Incidentally, when using the check valve CV as depicted in another configuration example in FIG. 9, the pump P1 is stopped, and the pump P2 is driven as well as the valve V3 is opened with the valve V1 closed, under the control of the control unit 2, in the filling operation as depicted in FIG. 10, thereby being able to perform the pump driven suction.

===Another Control Example of Dispensing Apparatus===

In an embodiment described above, although the dispensing device discharges substantially all of the liquid in the syringe 1 by performing the dispensing operation 1, after discharging a small amount of the liquid in the syringe 1 by performing the dispensing operation 2 when starting dispensing, it is not limited thereto. For example, as depicted in FIG. 13, the dispensing operation 2 may be further performed after the dispensing operation 1.

Figure 13:
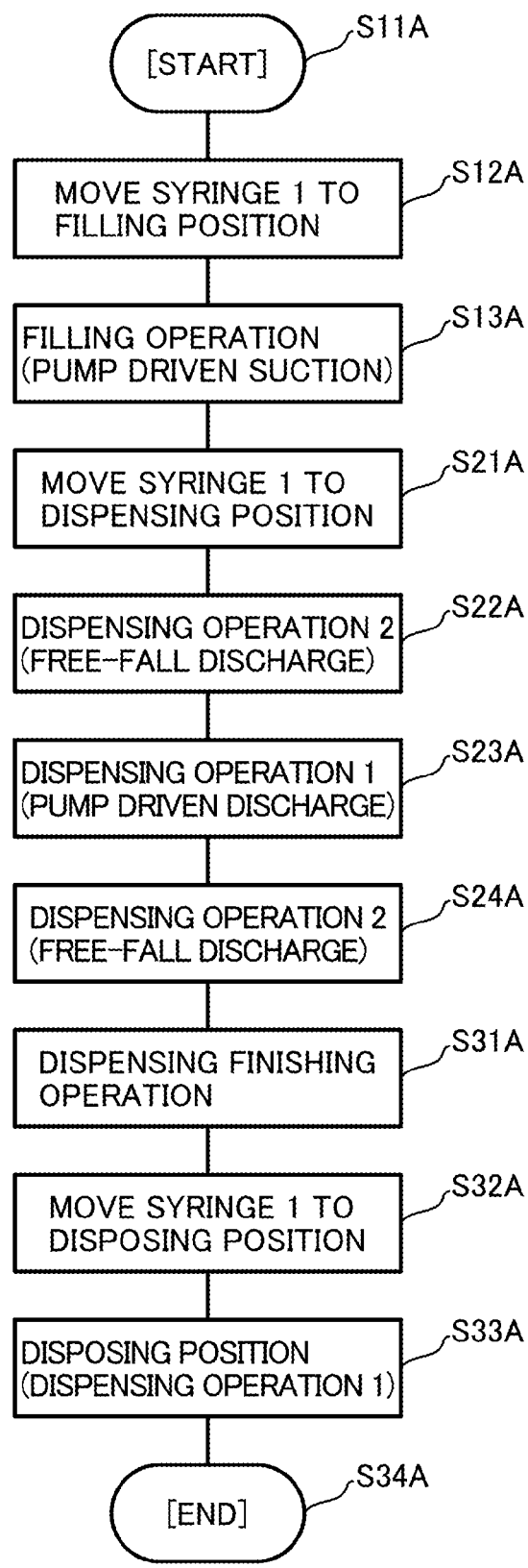
FIG. 13 is an exemplary flowchart explaining another control example of a dispensing device.
Figure 14:
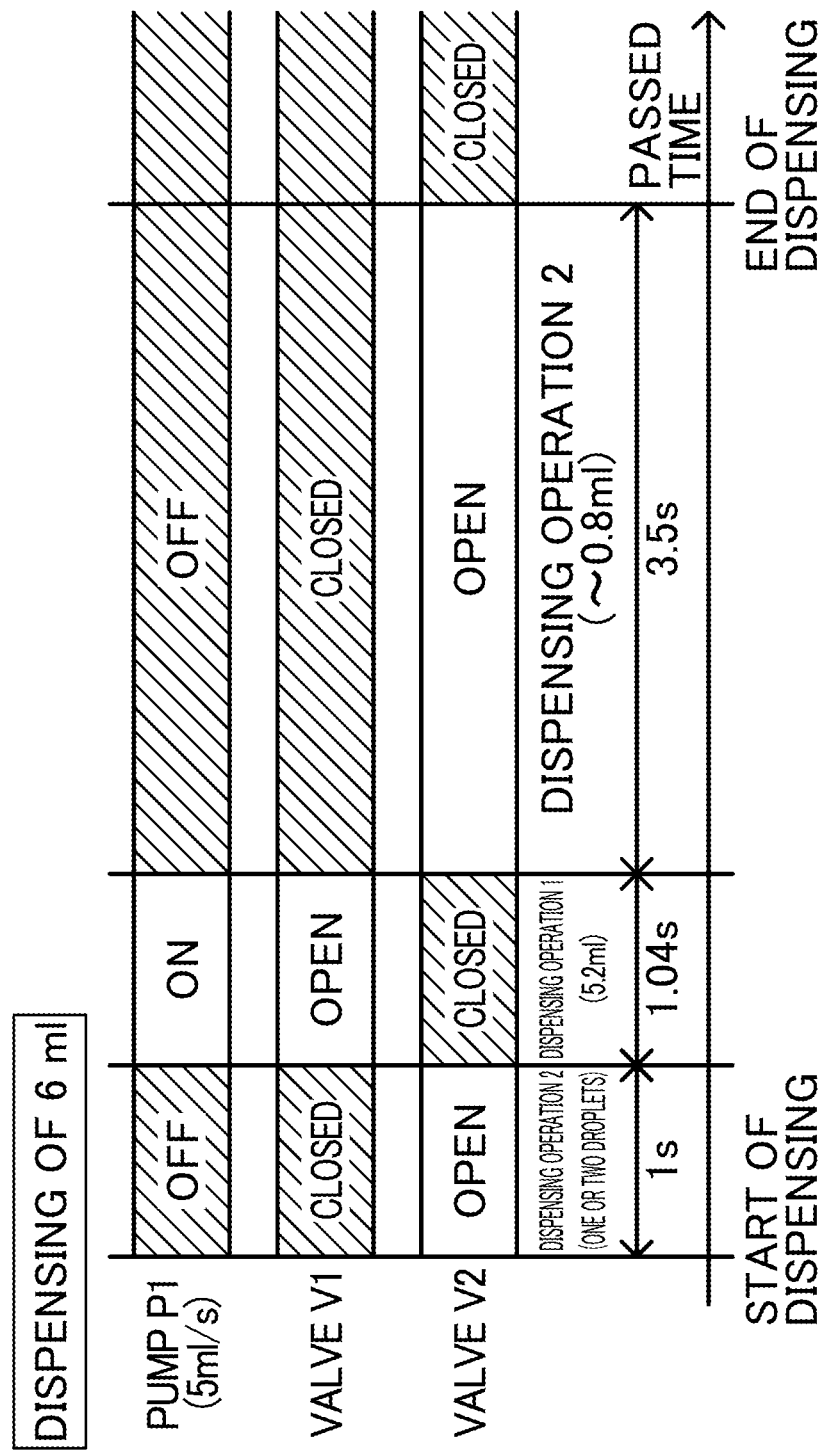
FIG. 14 is an exemplary view of a diagram illustrating an example of operation times of dispensing operations 1 and 2 when dispensing 6 ml of a liquid under control illustrated in FIG. 13.

Here, FIG. 14 illustrates each operation time of the dispensing operations 1 and 2 when dispensing 6 ml of the liquid under the control depicted in FIG. 13 using the pump P1, which is configured to discharge the liquid at 5 ml/s, by way of example. In FIG. 14, when starting dispensing, a small amount (about one drop or two) of the liquid in the syringe 1 runs out from the nozzle 11 by performing the dispensing operation 2 for one second, similarly to FIG. 16. Further, by subsequently performing the dispensing operation 1 for 1.04 seconds, substantially all (a little under 90%) of the liquid in the syringe 1 is discharged from the nozzle 11. Furthermore, the dispensing operation 2 is subsequently performed for 3.5 seconds, thereby causing substantially all of the remaining liquid (a little over 10%) in the syringe 1 to run out from the nozzle 11.

Note that, in the final dispensing operation 2, a very small amount of the liquid can remain in the syringe 1 or the nozzle 11 by the surface tension of the liquid. Thus, bubbles, which would be generated when the final droplet of the liquid were forcibly discharged by the pump driven discharge, and/or splatters, which would be generated by the burst of the bubble, can be suppressed. Further, the inner diameter of the discharge port (tip) of the nozzle 11 is set in consideration of the surface tension of the dispensing liquid, and the like. In an embodiment of the present disclosure, the inner diameter is assumed to be approximately 0.25 mm to 5.0 mm, by way of example.

Further, in an embodiment of the present disclosure, the amount of the liquid to be discharged by the dispensing operation 1 is set in consideration of an error in fluid delivery volume in the pump. For example, when an error in the fluid delivery volume is within ±10%, the amount is set such that a little under 90% of the whole discharge amount is to be discharged by the dispensing operation 1, so that the amount corresponding to the error in the fluid delivery volume remains in the syringe 1 without the whole amount of the liquid being discharged by the pump driven discharge. Thus, generation of the bubbles and/or splatters can be avoided, which would be generated if the pump driven discharge were performed to the end.

As such, in the control flow illustrated in FIG. 13, the dispensing operation 2 is performed when starting dispensing, the dispensing operation 1 is performed after the dispensing operation 2, and the dispensing operation 2 is further performed after the dispensing operation 1. Therefore, it becomes possible to gradually dispense only the liquid in the free-fall discharge after quick dispensing by the pump driven discharge, thereby being able to suppress generation of the splatters and bubbles at the end of the dispensing and prevent contamination of something other than the liquid dispensing target.

As has been described, in the dispensing device depicted in FIG. 1 and FIG. 9, the dispensing operation 2 is performed at the start of dispensing and the dispensing operation 1 is performed after the dispensing operation 2, thereby being able to gradually start dispensing in the free-fall discharge and perform the pump driven discharge after the removal of the gas phase at the tip of the nozzle 11. Thus, generation of the splatter and bubble at the start of dispensing can be suppressed, and contamination of something other than the liquid dispensing target can be prevented.

Further, in the dispensing device depicted in FIG. 1, the control unit 2 controls the valve V1 configured to open/close the (first) flow path between the syringe 1 and the pump P1 for discharge; and the valve V2 configured to open/close the (second) flow path between the syringe 1 and external air, thereby being able to perform the pump driven discharge after reliably performing the free-fall discharge.

Further, generation of splatter or bubble at the end of the dispensing can be suppressed, and contamination of something other than the liquid dispensing target can be prevented, by further performing the dispensing operation 2 after the dispensing operation 1.

Further, in the dispensing device illustrated in FIG. 9, the control signal Sv2 for controlling the second valve, which is to be outputted from the control unit 2, can be reduced by adopting the check valve CV, which is configured to open/close the (second) flow path between external air and the flow path between the valve V1 and the pump P1 for discharge, and allow external air to flow in but prevent air from flowing out to external air.

Further, the control unit 2 further controls the valve V3 configured to open/close the (third) flow path between the syringe 1 and the pump P2 for suction, thereby being able to perform a series of filling/dispensing operations including a filling operation and a dispensing operation.

Further, a large part of the liquid in the syringe 1 is dispensed by the pump driven discharge and thereafter the remaining liquid in the syringe 1 is dispensed in the free-fall discharge, thereby being able to reduce the time period required for the dispensing operation while preventing the contamination of something other than the liquid dispensing target.

Further, in the dispensing system depicted in FIG. 2, the syringe drive portion 3 and the dish drive portion 4 can relatively move the syringe 1 (nozzle 11) to the dispensing position, by controlling the relative position between the syringe 1 (nozzle 11) and the liquid dispensing target.

Note that the above embodiments of the present disclosure are simply for facilitating the understanding of the present disclosure and are not in any way to be construed as limiting the present disclosure. The present disclosure may variously be changed or altered without departing from its spirit and encompass equivalents thereof.

In an embodiment of the present disclosure, a description has been given of the case where the cell culture apparatus is used as an example of the application of the dispensing system including the dispensing device, but it is not limited thereto. The liquid to be dispensed by the dispensing device may be other liquid, such as ink or adhesive, which needs to be prevented from contaminating something other than the liquid dispensing target.

What is claimed is:

1. A dispensing device comprising:
a syringe including a nozzle;
a first pump configured to generate a pressure to discharge a liquid in the syringe through the nozzle;
a second pump configured to generate a pressure to draw a liquid into the syringe through the nozzle;
a first valve configured to open and close a first flow path between the syringe and the first pump;
a second valve configured to open and close a second flow path between the syringe and external air;
a third valve configured to open and close a third flow path between the syringe and the second pump; and
a controller configured to:
control the first pump, the first valve and the second valve to discharge the liquid in the syringe through the nozzle, and when discharging the liquid in the syringe, close the second valve, drive the first pump, and open the first valve to discharge a part of the liquid in the syringe with the pressure generated by the first pump from the nozzle, and thereafter stop the first pump, close the first valve, and open the second valve to allow the liquid in the syringe to flow out at its own weight from the nozzle, and
when drawing the liquid into the syringe, drive the second pump and open the third valve to draw the liquid into the syringe with the pressure generated by the second pump.

2. The dispensing device according to claim 1, wherein the controller is further configured to, when discharging the liquid in the syringe, discharge a large part of the liquid in the syringe with the pressure generated by the first pump, and thereafter allows the liquid in the syringe to flow out at its own weight.

3. A dispensing system comprising:
the dispensing device according to claim 1; and
a drive portion configured to relatively move the syringe to a position at which the liquid in the syringe is to be dispensed to a target, by moving at least one of the syringe and the target to which the liquid in the syringe is to be dispensed.

4. A dispensing device comprising:
a syringe including a nozzle;
a first pump configured to generate a pressure to discharge a liquid in the syringe through the nozzle;
a first valve configured to open and close a first flow path between the syringe and the first pump;
a second valve configured to open and close a second flow path between external air and the first flow path, the second flow path being connected to a location of the first flow path between the first pump and the first valve in the first flow path, to allow gas to flow from external air to the first flow path through the second flow path and to prevent gas from flowing out from the first flow path to external air through the second flow path; and
a controller configured to control the first pump, the first valve and the second valve to discharge the liquid in the syringe through the nozzle, and when discharging the liquid in the syringe, close the second valve, drive the first pump, and open the first valve to discharge a part of the liquid in the syringe with the pressure generated by the first pump, and thereafter stop the first pump, close the first valve, and open the second valve to allow the liquid in the syringe to flow out at its own weight from the nozzle.

5. A dispensing device comprising:
a syringe including a nozzle;
a first pump configured to generate a pressure to discharge a liquid in the syringe through the nozzle;
a first valve configured to open and close a first flow path between the syringe and the first pump;
a second valve configured to open and close a second flow path between the syringe and external air; and
a controller configured to control the first pump, the first valve and the second valve to discharge the liquid in the syringe through the nozzle, and when discharging the liquid in the syringe, maintain the first pump to be stopped, close the first valve, and open the second valve to allow a part of the liquid in the syringe to flow out at its own weight from the nozzle, and thereafter close the second valve, drive the first pump, and open the first valve to discharge the liquid in the syringe with the pressure generated by the first pump.

6. The dispensing device according to claim 5, wherein the control unit is further configured to, when discharging the liquid in the syringe, allow a part of the liquid in the syringe to flow out at its own weight, discharge another part of the liquid in the syringe with the pressure generated by the first pump, and thereafter allow the liquid in the syringe to flow out at its own weight.

7. The dispensing device according to claim 5, further comprising:
   a second pump configured to generate a pressure to draw the liquid into the syringe through the nozzle; and
   a third valve configured to open and close a third flow path between the syringe and the second pump, wherein
   the controller is further configured to, when drawing the liquid into the syringe, drive the second pump and open the third valve to draw the liquid into the syringe with the pressure generated by the second pump.

8. A dispensing system comprising:
   the dispensing device according to claim 5; and
   a drive portion configured to relatively move the syringe to a position at which the liquid in the syringe is to be dispensed to a target, by moving at least one of the syringe and the target to which the liquid in the syringe is to be dispensed.

9. A dispensing device comprising:
   a syringe including a nozzle;
   a first pump configured to generate a pressure to discharge a liquid in the syringe through the nozzle;
   a first valve configured to open and close a first flow path between the syringe and the first pump;
   a second valve configured to open and close a second flow path between external air and the first flow path, the second flow path being connected to a location of the first flow path between the first pump and the first valve in the first flow path, to allow gas to flow from external air to the first flow path through the second flow path and to prevent gas from flowing out from the first flow path to external air through the second flow path; and
   a controller configured to, when discharging the liquid in the syringe, maintain the first pump to be stopped and open the first valve to allow a part of the liquid in the syringe to flow out at its own weight from the nozzle, and thereafter drive the first pump with the first valve being open, to discharge the liquid in the syringe with the pressure generated by the first pump.

* * * * *